(12) United States Patent
Fischkoff et al.

(10) Patent No.: US 7,611,702 B2
(45) Date of Patent: Nov. 3, 2009

(54) TNF-ALPHA BLOCKER TREATMENT FOR ENTEROCOLITIS ASSOCIATED WITH IMMUNOSTIMULATORY THERAPEUTIC ANTIBODY THERAPY

(75) Inventors: Steven Fischkoff, Short Hills, NJ (US); Israel Lowy, Dobbs Ferry, NY (US); Michael Yellin, Montclair, NJ (US); James Chung-Yin Yang, Silver Spring, MD (US)

(73) Assignee: Medarex, Inc., Princeton, NJ (US)

( * ) Notice: Subject to any disclaimer, the term of this patent is extended or adjusted under 35 U.S.C. 154(b) by 0 days.

(21) Appl. No.: 11/557,835

(22) Filed: Nov. 8, 2006

(65) Prior Publication Data

US 2007/0248595 A1 Oct. 25, 2007

Related U.S. Application Data

(60) Provisional application No. 60/734,963, filed on Nov. 8, 2005.

(51) Int. Cl.
*A61K 39/395* (2006.01)
*A61K 38/16* (2006.01)
*C07K 16/28* (2006.01)
*C07K 16/46* (2006.01)

(52) U.S. Cl. .............. 424/130.1; 424/134.1; 530/387.1; 530/387.3

(58) Field of Classification Search .................. None
See application file for complete search history.

(56) References Cited

U.S. PATENT DOCUMENTS

| 5,656,272 | A | 8/1997 | Le et al. |
| 5,811,097 | A | 9/1998 | Allison et al. |
| 5,855,887 | A | 1/1999 | Allison et al. |
| 6,207,156 | B1 | 3/2001 | Kuchroo et al. |
| 6,682,736 | B1 | 1/2004 | Hanson et al. |
| 6,984,720 | B1 | 1/2006 | Korman et al. |
| 2002/0086014 | A1 | 7/2002 | Korman et al. |
| 2004/0241169 | A1 | 12/2004 | Lowy et al. |
| 2005/0201994 | A1 | 9/2005 | Korman et al. |

FOREIGN PATENT DOCUMENTS

| WO | WO9842752 | 10/1998 |
| WO | WO0037504 | 6/2000 |
| WO | WO0114424 | 3/2001 |

OTHER PUBLICATIONS

Huang Z., Pharmacology and Therapeutics, 2000, 86: 201-215.*
Phan et al., PNAS, 2003, 100: 8372-8377.*
Van Assche et al., Curr. Opin. Gastroenterol., Jul. 2005, 21: 443-447.*
Gray et al., Clinical Science, 2006, 111: 93-106 (privided by Applicant).*
Hochberg et al., Semin. Arthritis Rheum, 2005, 34: 819-836 (provided by Applicant).*
Spencer et al., Gastroenterology, 2002, 122: 94-109 (provided by Applicant).*
Brown et al., 2002, Arthritis and Rheumatism, 46: 3151-3158 (provided by Applicant).*
Balzano et al., "CTLA-4 and CD28: similar proteins, neighbouring genes," Int J Cancer Suppl. 1992;7:28-32.
Hurwitz et al., "CTLA-4 blockade synergizes with tumor-derived granulocyte-macrophage colony-stimulating factor for treatment of an experimental mammary carcinoma," Proc Natl Acad Sci U S A. Aug. 18, 1998;95(17):10067-71.
Mokyr et al., "Realization of the therapeutic potential of CTLA-4 blockade in low-dose chemotherapy-treated tumor-bearing mice," Cancer Res. Dec 1, 1998;58(23):5301-4.
Murata et al., "Expression of the costimulatory molecule BB-1, the ligands CTLA-4 and CD28, and their mRNA in inflammatory myopathies," Am J Pathol. Aug. 1999;155(2):453-60.
Camacho et al. (2004). J. Clin. Oncology. 22(145):abstract No. 2505, "Phase 1 clinical trial of anti-CTLA4 human monoclonal antibody CP-675,206 in patients (pts) with advanced solid malignancies".

* cited by examiner

*Primary Examiner*—Ilia Ouspenski
(74) *Attorney, Agent, or Firm*—Baker Botts L.L.P.

(57) ABSTRACT

The present invention provides methods for treating adverse events related to immunotherapy. More specifically, the present invention provides methods for treating the enterocolitis associated with anti-CTLA-4 antibody immunotherapy.

20 Claims, 3 Drawing Sheets

A.  B.  C.

TNF-ALPHA BLOCKER TREATMENT FOR ENTEROCOLITIS ASSOCIATED WITH IMMUNOSTIMULATORY THERAPEUTIC ANTIBODY THERAPY

RELATED APPLICATIONS

This application claims priority to U.S. Provisional application Ser. No. 60/734,963, filed on Nov. 8, 2005, the contents of which are expressly incorporated herein by reference.

FIELD OF THE INVENTION

The present invention relates to the field of treating adverse events from immunotherapy. More specifically, the present invention relates to methods for treating enterocolitis associated with anti-CTLA-4 antibody immunotherapy.

BACKGROUND

Immune-related adverse events are a frequently observed consequence of immunostimulatory antibody therapy. These immune-related adverse events, which can be severe, and even life-threatening, include autoimmune responses, such as diarrhea, enterocolitis, dermatitis, hypophysitis, panhypopituitarism, rash, pruritis, and vitiligo (see, e.g., U.S. Patent Publication No. 2004/0241169 A1).

Anti-CTLA-4 antibodies are known immunostimulatory agents (see, e.g., PCT Publication Nos. WO 01/14424 and WO 00/37504, which describe human sequence anti-human CTLA-4 antibodies). Non-human CTLA-4 antibodies have been used in the various studies. U.S. Pat. No. 5,855,887 discloses a method of increasing the response of a mammalian T cell to antigenic stimulation by combining a T cell with a CTLA-4 blocking agent. U.S. Pat. No. 5,811,097 discloses a method of decreasing the growth of non-T cell tumors by administering a CTLA-4 blocking agent. U.S. patent application Ser. Nos. 09/644,668 and 09/948,939 disclose human CTLA-4 antibodies. Each of these patents and applications is hereby incorporated by reference.

Therapy with an immunostimulatory agent, such as an anti-CTLA-4 antibody, is associated with certain adverse events, which appear to be mediated by the immune system. For example, adverse events related to MDX-010 (see PCT Publication No. WO 01/1424) therapy appear to have an immune etiology and may be a consequence of the intrinsic biological activity of MDX-010. These adverse events may be due to a loss of tolerance to some self-antigens or an exaggerated reaction to foreign antigens (e.g., gut bacteria). Although skin adverse events are most common, the most clinically significant immune-related adverse event following MDX-010 therapy is diarrhea secondary to enterocolitis. The enterocolitis observed following MDX-010 therapy is grossly (e.g., endoscopically) and histologically similar to inflammatory bowel disease. The gross and microscopic characteristics of ulcerative colitis and Crohn's disease are well-known. See, e.g., Harrison's Principles of Internal Medicine (15$^{th}$ ed. 2001) pp. 1681-1685. In most cases, this immune-related enterocolitis resolves with symptomatic treatment including intravenous hydration and high-dose parenteral steroids. In certain cases, however, the enterocolitis associated with immunostimulatory therapeutic antibody induced enterocolitis is refractory to steroid therapy.

Interestingly, in one study, almost 45% of patients developing an autoimmune-like adverse event also experienced a clinical response, including a patient with hypopituitarism, who demonstrated a durable complete response. These adverse events, likely reflect a loss of tolerance to some self antigens, or a hyper-response to bacterial antigens present in the gut or skin, and are therefore mechanism-related and may be directly linked to the clinical antitumor activity of MDX-010.

Accordingly, it would be desirable to provide methods for effective treatment of adverse events, which can accompany immunostimulatory therapeutic antibody, e.g., anti-CTLA-4 antibody, treatment of a disease or condition. In particular, a need exists for treatment of immune-related enterocolitis following immunostimulatory therapeutic antibody treatment, which does not interfere with the desired immune enhancement (e.g., anti-tumor immunity).

SUMMARY OF THE INVENTION

The present invention advantageously provides a method for treating enterocolitis induced by an immunostimulatory therapeutic antibody in a patient through the administration of an effective amount of a TNF-α blocker to the patient. In an embodiment of the invention, the enterocolitis induced by an immunostimulatory therapeutic antibody is refractory to steroid treatment. In another embodiment, the immunostimulatory therapeutic antibody is an anti-CTLA-4 antibody.

The methods and compositions of the present invention provide treatment for immunostimulatory therapeutic antibody-induced enterocolitis which, in turn, permits a greater number of patients to complete immunotherapy.

In one aspect of the invention, first-line treatment of a patient with immunostimulatory therapeutic antibody induced enterocolitis with a TNF-α blocker, instead of a systemic steroid, can avoid any adverse effect on the antitumor effect of the antibody due to the immunosuppressive effect of the steroid.

In another aspect of the invention, second-line treatment of a patient with steroid-refractory immunostimulatory therapeutic antibody induced enterocolitis with a TNF-α blocker can avoid major morbidity (e.g., major surgery) or even death.

Thus, the invention relates in one embodiment to a method for treating enterocolitis induced by an immunostimulatory therapeutic antibody in a patient, which method comprises administering an effective amount of a TNF-α blocker.

The invention further provides for use of a TNF-α blocker in the manufacture of a medicament for treating enterocolitis induced by an immunostimulatory therapeutic antibody, e.g., in accordance with the foregoing methods.

A particular advantage of the invention results from a method for treating the inflammation of the gastrointestinal tract by an immunostimulatory therapeutic antibody in a patient. In some instances, administration of the therapeutic antibody can lead to inflammation of the gastrointestinal tract, which results in diarrhea. The method of the present invention comprises administering an effective amount of a TNF-α blocker to the patient in order to treat enterocolitis induced by an immunostimulatory therapeutic antibody in a patient, and use of such a TNF-α blocker in the manufacture of a medicament to treat such enterocolitis.

In an aspect of the foregoing methods, the antibody is an anti-CTLA-4 antibody, particularly a human sequence antibody that binds to human CTLA-4. In specific examples described herein, the anti-CTLA-4 antibody is antibody 10D1 (MDX-010).

All aspects of the invention pertain to any therapeutic administration of an immunostimulatory antibody, particularly an anti-CTLA-4 antibody. In specific embodiments, the anti-CTLA-4 antibody is administered for the treatment of malignant melanoma, prostate cancer or ovarian cancer.

DETAILED DESCRIPTION

Figure 1:
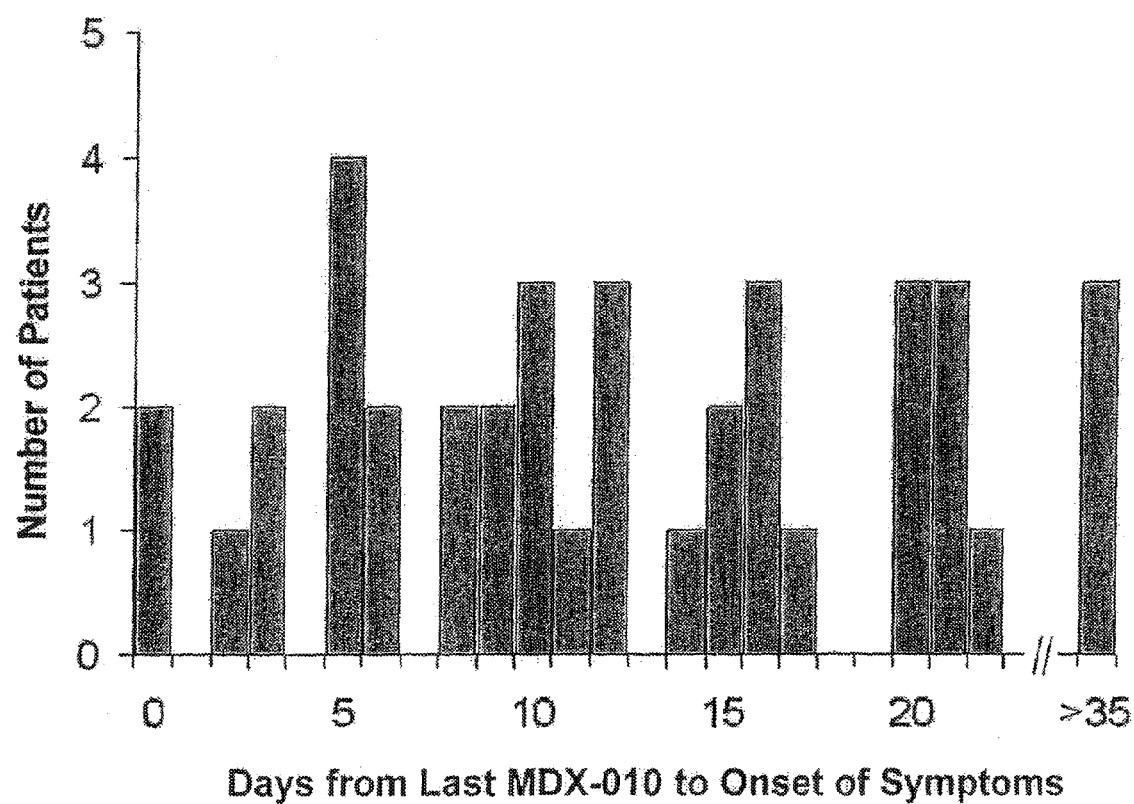
FIG. 1 is a bar graph showing the number of days from the last dose of anti-CTLA-4 antibody MDX-010 administration to a patient to the onset of symptoms of enterocolitis.

The present invention is based, in part, on results with 198 patients with metastatic melanoma (MM) or renal cell carcinoma (RCC) who have been treated with MDX-010 alone or combined with vaccination. The overall tumor response rate in these patients was 15%. Immune mediated toxicities related to the MDX-010 therapy were observed and included: dermatitis, enterocolitis, hypophysitis, uveitis, hepatitis, and nephritis. Enterocolitis (defined by Grade III/IV clinical presentation and/or biopsy documentation) was the most common major toxicity with an incidence of 21%. This enterocolitis presented with diarrhea and showed both neutrophil- and lymphocyte-predominant histology. Most patients who developed enterocolitis responded to high-dose systemic corticosteroids. However, five patients did not respond to steroids and suffered perforated colons or required colectomy. Four patients with steroid-refractory enterocolitis responded promptly to TNF-α blockade with infliximab. Objective tumor response rates in patients with enterocolitis were 38% for MM and 46% for RCC compared to 12% and 2% in patients without enterocolitis, respectively (p=0.0063 for MM and p=0.0004 for RCC).

As used herein, a "TNF-α blocker" is any molecule that inhibits the activity resulting from the binding of TNF-α with its receptor. In an embodiment of the invention, a TNF-α blocker is an anti-TNF-α antibody. Particular TNF-α blockers of the invention include, for example, infliximab, etanercept, certolizumab pegol (CDP870), golimumab and adalimumab.

As used herein, an "immunostimulatory therapeutic molecule" is any molecule (e.g., small molecule, protein, peptide, nucleic acid molecule, or antibody) that is administered to a patient to stimulate the patient's immune system for the purpose of treating a disease (e.g., a cancer or infectious disease). As used herein, an "immunostimulatory therapeutic antibody" is a subset of an immunostimulatory therapeutic molecule and is any antibody that is administered to a patient to stimulate the patient's immune system for the purpose of treating a disease (e.g., a cancer or infectious disease). In particular, the invention relates to an anti-CTLA-4 antibody. In a specific embodiment, the antibody is specific for human CTLA-4. In a further embodiment, the antibody is a human sequence antibody, e.g., antibody 10D1 as disclosed in PCT Publication No. WO 01/14424.

As used herein, "enterocolitis" is an inflammatory condition of the colon (i.e., the large intestine) and/or small intestine that can be associated with symptoms such as diarrhea, cramping, abdominal pain, bloating and/or constipation; or signs such as a bowel (e.g., colon) wall that is edematous, hyperemic, and/or friable (as observed, for example, during an endoscopic examination).

As used herein, "enterocolitis induced by an immunostimulatory therapeutic antibody" means an enterocolitis that: (1) has its first occurrence in a patient concurrent with, or shortly after (i.e., days or weeks), administration of an immunostimulatory therapeutic antibody, and (2) is identified as an enterocolitis induced by an immunostimulatory therapeutic antibody by a physician, or (3) is not identified as an enterocolitis of another etiology (e.g., *Clostridium difficile* toxin) by a physician.

As used herein, the terms "refractory to steroid treatment" and "steroid refractory enterocolitis" refer to enterocolitis induced by an immunostimulatory therapeutic antibody that is unresponsive to steroid therapy.

Except when noted, the terms "patient" or "subject" are used interchangeably and refer to mammals such as human patients and non-human primates, as well as experimental animals such as rabbits, rats, and mice, and other animals. Animals include all vertebrates, e.g., mammals and non-mammals, such as sheep, dogs, cows, chickens, amphibians, and reptiles. Usually such patient is receiving an immunostimulatory antibody, e.g., an anti-CTLA-4 antibody, to treat a disease or condition. PCT Publication No. WO 01/14424 sets forth diseases and conditions treatable with an anti-CTLA-4 antibody, including but not limited to malignant melanoma, prostate cancer, and ovarian cancer. The present specification incorporates by reference the subject matter disclosed in PCT Publication No. WO 01/14424 relating to disease treatment.

As used herein, the terms "treat," "treating," and "treatment" relate to the administration of a TNF-α blocker of the present invention to prevent or delay the onset of the symptoms, complications, or biochemical indicia of immunostimulatory therapeutic antibody induced enterocolitis; alleviate the symptoms or arrest or inhibit further development of this enterocolitis. Treatment may be prophylactic (to prevent or delay the onset of the disease, or to prevent the manifestation of clinical or subclinical symptoms thereof) or therapeutic suppression or alleviation of symptoms after the manifestation of the enterocolitis.

The terms "cytotoxic T lymphocyte-associated antigen-4," "CTLA-4," "CTLA4," "CTLA-4 antigen" and "CD152" (see, e.g., Murata, Am. J. Pathol. 1999;155:453-460) are used interchangeably, and include variants, isoforms, species homologs of human CTLA-4, and analogs having at least one common epitope with CTLA-4 (see, e.g., Balzano (1992) Int. J. Cancer Suppl. 7:28-32). The complete sequence of CTLA-4 is found in GenBank Accession No. L15006.

The phrase "immune cell response" refers to the response of immune system cells to external or internal stimuli (e.g., antigen, cytokines, chemokines, and other cells) producing biochemical changes in the immune cells that result in immune cell migration, killing of target cells, phagocytosis, production of antibodies, other soluble effectors of the immune response, and the like.

The term "immune response" refers to the concerted action of lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

MDX-010 Therapy

The human monoclonal antibody MDX-010 (Medarex, Inc.) in clinical development corresponds to monoclonal antibody 10D1, which is disclosed in U.S. Patent Publication No. 2005/0201994, PCT Publication No. WO 01/14424, U.S. Pat. No. 6,984,720, and U.S. Patent Publication No. 2002/086014. MDX-101 is also referred to as ipilimumab. MDX-010 has been administered as single or multiple doses, alone or in combination with a vaccine, chemotherapy, or interleukin-2 to greater than 500 patients diagnosed with metastatic melanoma, prostate cancer, lymphoma, renal cell cancer, breast cancer, ovarian cancer, and HIV.

Other anti-CTLA-4 antibodies that can be used in a method of the present invention include, for example, those disclosed in: WO 98/42752; WO 00/37504; U.S. Pat. Nos. 6,682,736; 6,207,156; Hurwitz et al., PNAS 1998;95(17):10067-10071; Camacho et al., J Clin Oncology 2004:22(145):abstract no. 2505 (antibody CP-675206); and Mokyr, et al., Cancer Research 1998;58:5301-5304.

The dosage and schedule for administration of an anti-CTLA-4 antibody used in a method of the present invention can be determined by one of skill in the art. For example, the dosage of the antibody can range from about 0.1 mg/kg to about 50 mg/kg, typically from about 1 mg/kg to about 25 mg/kg. In particular embodiments, the anti-CTLA-4 antibody dosage is 1 mg/kg, 3 mg/kg, 5 mg/kg, 10 mg/kg, 15 mg/kg, 20 mg/kg or 25 mg/kg. The dosage schedule for administration of the antibody can vary depending on the desired aggressiveness of the therapy, as determined by the practitioner. Dosages and dosage schedules are described in U.S. Patent Publication No. 20020086014. In a specific embodiment, the dosage of anti-CTLA-4 antibody is 10 mg/kg.

Enterocolitis Associated With Anti-CTLA-4 Antibody Therapy

Organs that most commonly exhibit immune-related adverse events following anti-CTLA-4 antibody therapy are the GI tract (e.g., diarrhea and colitis) and the skin (e.g., rash and pruritis). Diarrhea following MDX-010 treatment can range from mild to severe, and can even be life-threatening. Colonic wall biopsies in patients with post-MDX-010 diarrhea have revealed pleomorphic infiltrates, which include many lymphocytes and are consistent with colitis due to an immune-mediated process. Most cases of diarrhea and enterocolitis resolve with symptomatic treatment (e.g., fluid replacement) or corticosteroid treatment.

Non-colonic gastrointestinal immune-related adverse events have also been observed in the esophagus (esophagitis), duodenum (duodenitis), and ileum (ileitis).

TNF-α Blockers

TNF-α blockers of the present invention include, for example, infliximab, etanercept, certolizumab pegol (CDP870), golimumab and adalimumab.

Infliximab (REMICADE®) (Centocor, Inc., Malvern, Pa.) is a chimeric monoclonal antibody that specifically binds to human TNF-α and inhibits the binding of TNF-α with its receptor. Infliximab is typically administered as an intravenous infusion. Infliximab is typically administered in a dosage of about 3 mg/kg to about 5 mg/kg. Infliximab can be administered in a single dose or multiple doses. For example, induction doses of 5 mg/kg infliximab can be administered intravenously at 0, 2 and 6 weeks followed by a maintenance dose of 5 mg/kg every 8 weeks thereafter until the enterocolits induced by an immunostimulatory therapeutic antibody resolves.

Etanercept (ENBREL®) (Immunex Corp., Thousand Oaks, Calif.) is a dimeric fusion protein that binds to TNF-α and blocks the binding of TNF-α to its receptor. Etanercept is typically administered by subcutaneous injection. Etanercept is typically administered in a dosage of about 50 mg per week. Etanercept can be administered in a single dose or multiple doses. For example, etanercept can be administered in a 50 mg dose twice weekly for 3 months followed by a maintenance dose of 50 mg once per week until the enterocolitis induced by an immunostimulatory therapeutic antibody resolves.

Certolizumab pegol (CDP870) (CIMZIA®) (UCB Pharma, Inc., Smyrna, Ga.) is a PEGylated Fab' fragment of a humanized anti-TNF-α antibody. Certolizumab pegol is typically administered by subcutaneous injection. Certolizumab pegol can be administered in a single dose or multiple doses.

Golimumab (CNTO 148) (Centocor, Inc.) is a human monoclonal antibody, which binds to and blocks the activity of TNF-α.

Adalimumab (HUMIRA®) is human monoclonal anti-TNF-α antibody that blocks the binding to TNF-α to its receptor. Adalimumab is typically administered by subcutaneous injection. Adalimumab is typically administered in a dosage of about 40 mg every other week. For example, adalimumab can be administered in a 40 mg dose every other week until the enterocolitis induced by an immunostimulatory therapeutic antibody resolves.

Dose

One of skill in the art can readily determine the effective amount of TNF-α blocker to be administered for use in a method of the present invention. In general, an effective amount of a TNF-α blocker according to the invention is the lowest amount required to produce a therapeutic effect, i.e., to treat enterocolitis induced by an immunostimulatory therapeutic antibody. One of skill in the art can consult the label of a TNF-α blocker for dosing information. The exact amount to be administered to a patient can vary depending on the state and severity of the disorder and the physical condition of the patient. A TNF-α blocker according to the invention can be administered in one daily dose or in divided doses.

According to the present invention, an immunostimulatory therapeutic antibody and a TNF-α blocker can be administered concurrently (e.g., on the same day). Alternatively, according to the present invention, the TNF-α blocker can be administered following the first dose of an immunostimulatory therapeutic antibody.

Routes of Administration

According to the invention, a TNF-α blocker can be formulated in a pharmaceutical composition to be administered parenterally, or transmucosally, e.g., orally, nasally, or rectally, or transdermally. Preferably, administration is via intravenous infusion or injection, or subcutaneous injection. Other routes of administration according to the invention include, but are not limited to, intra-arteriole, intramuscular, intradermal, and intraperitoneal administration.

EXAMPLES

The present invention is also described by means of the following examples. However, the use of these or other examples anywhere in the specification is illustrative only and in no way limits the scope and meaning of the invention or of any exemplified term. Likewise, the invention is not limited to any particular preferred embodiments described herein. Indeed, many modifications and variations of the invention may be apparent to those skilled in the art upon reading this specification and can be made without departing from its spirit and scope. The invention is therefore to be limited only by the terms of the appended claims along with the full scope of equivalents to which the claims are entitled.

Example 1

Clinical Study of Patients Treated With Anti-CTLA-4 Antibody 198 patients with Stage IV melanoma or Stage IV clear cell renal carcinoma were treated with intravenous human anti-CTLA-4 monoclonal antibody (MDX-010, Medarex, Inc., Princeton, N.J.). Melanoma patients were treated with MDX-010 and vaccine for melanoma (56 patients), or MDX-010 with dose escalation with or without vaccine (81 patients). Renal cell carcinoma patients were treated with MDX-010 alone (61 patients). MDX-010 was administered intravenously every three weeks in doses ranging from 1 mg/kg to 9 mg/kg. Vaccines used included modified gp100: 209-217 (210M) and gp100: 280-288 (288V) peptide vaccines (provided by Cancer Therapy Evaluation Program, NCI) emulsified with Montanide ISA 51 and injected subcutaneously every three weeks at the time of MDX-010 dosing.

Assessment of enterocolitis was variable in the first 10 patients who presented with this adverse event. One additional patient presented to an outside hospital with colonic perforation and no preceding symptoms. The remaining 30 patients with enterocolitis were evaluated promptly upon the onset of diarrhea. Patients were made NPO and given intravenous (IV) hydration. Stool was sent for standard microbiological and parasite examination to rule out an infectious etiology. Colonoscopy or flexible sigmoidoscopy with biopsies was performed in 40 of the 41 patients. Many patients also underwent esophagogastroduodenoscopy (EGD) with biopsies. Patients were considered to have enterocolitis induced by the anti-CTLA-4 antibody therapy if they had biopsy findings showing enterocolitis or a clinical scenario of sudden onset diarrhea with no alternate etiology identified.

The first 10 patients who developed enterocolitis were treated with a variety of treatment regimens. A standardized, high-dose steroid regimen was developed when enterocolitis was recognized as a toxicity of MDX-010. Nearly all remaining patients were treated with this regimen, which consisted of intravenous dexamethasone 4 mg every 6 hours. High-dose steroids were continued for approximately 7 days followed by a taper over 17 days. Four patients with refractory enterocolitis were treated with a single dose of infliximab at 5 mg/kg. One patient received infliximab as the sole therapy for enterocolitis.

Enterocolitis: Forty-one patients were diagnosed with enterocolitis for an overall incidence of 21%. Incidence by protocol was: 14% for MDX-010 and vaccine (melanoma patients); 20% for MDX-010 dose escalation with or without vaccine (melanoma patients); and 28% for MDX-010 alone (no dose escalation) (renal cell carcinoma patients).

Presenting Symptoms: Patients presented with symptoms including abdominal pain, nausea and vomiting, fever, anal pain, and diarrhea. See Table 1.

TABLE 1

| Presenting symptom | No. of patients |
|---|---|
| Diarrhea | 40 |
| Abdominal pain | 8 |
| Nausea/vomiting | 6 |
| Fever | 5 |
| Anal pain | 4 |
| Rectal bleeding | 1 |
| Constipation | 1 |

Figure 2:
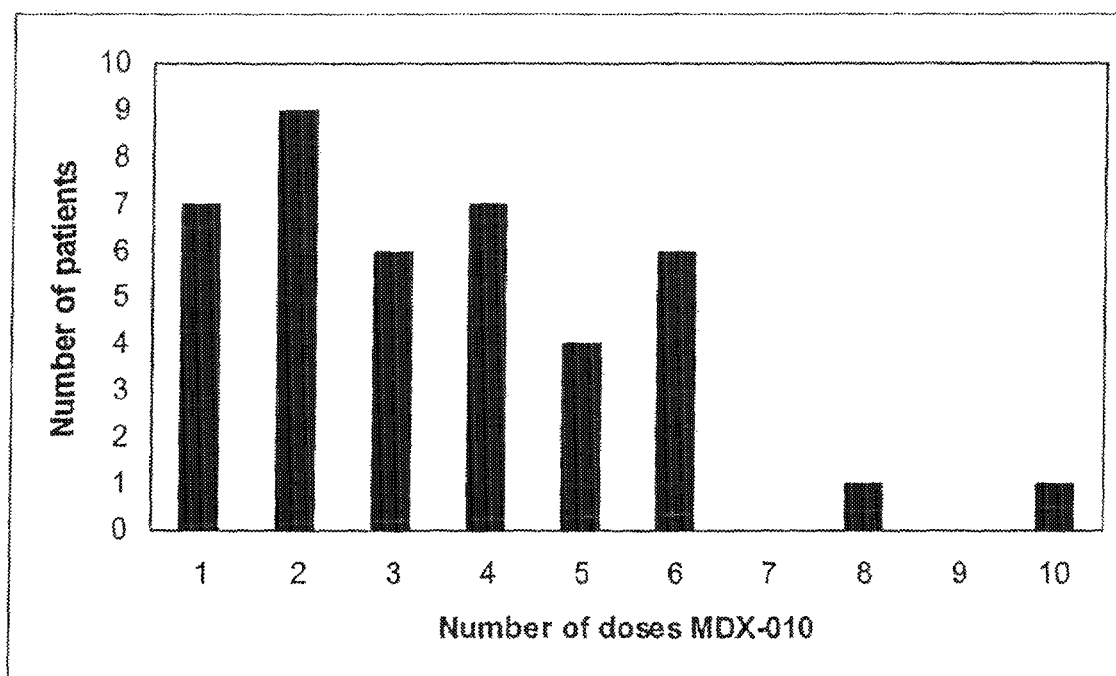
FIG. 2 is a bar graph showing the number of doses of anti-CTLA-4 antibody MDX-010 administered to a patient prior to the onset of enterocolitis.

Eighty-six percent of patients presented for treatment within 7 days of the onset of symptoms. For the 39 patients with available data, the median number of days from the last dose of MDX-010 to the onset of symptoms was 11 days (range 0-59 days). All but 4 patients developed symptoms within 21 days of their last dose. See FIG. 1. Patients received between 1 and 10 doses of MDX-010 prior to the onset of enterocolitis. See FIG. 2.

Endoscopic Findings: Forty patients underwent flexible sigmoidoscopy or colonoscopy with biopsies. Reports of gross findings were available for 36 patients. Twenty-three had the gross appearance of colitis (erythema, ulceration). The majority of patients (36/40) had histologically demonstrated colitis, including all 23 patients with gross findings of colitis. One additional patient was diagnosed with colitis retrospectively from a surgical specimen after a colectomy for colonic perforation. Eighteen patients underwent EGD as well. Reports were available for 16 of the patients who had EGD, and 10 showed grossly positive EGDs. Fourteen patients had histologically demonstrated gastritis or enteritis on pathological review, including two patients with negative colon biopsies. Two patients did not have histological findings of enterocolitis, but were diagnosed based on their persistent clinical symptoms.

Figure 3:
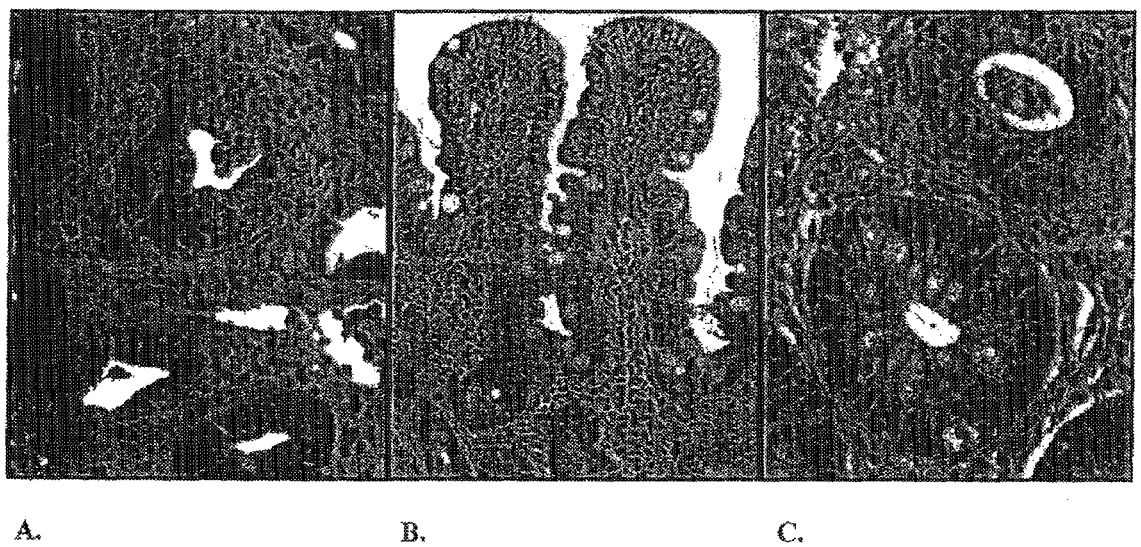
FIG. 3 shows three patterns of enterocolitis observed in the biopsies from the stomach, duodenum, colon, and rectum of patients: neutrophilic inflammation only (FIG. 3A), lymphocytic inflammation only (FIG. 3B), and combined neutrophilic and lymphocytic inflammation (FIG. 3C).

Histopathology: Three patterns of enterocolitis were observed in the biopsies from the stomach, duodenum, colon, and rectum: neutrophilic inflammation only, lymphocytic inflammation only, and combined neutrophilic and lymphocytic inflammation. See FIG. 3. Forty-four percent of the cases had a neutrophilic infiltration only. In the majority of these cases, neutrophilic involvement of the crypts (cryptitis) was observed with crypt abscesses present in 33% of the cases. Occasional cases showed eosinophils as the major component of the cryptitis or crypt abscess. Granulomas were present in 3 cases. The lamina propria showed increased CD4+T cells in 78% of the cases, and increased CD8+T cells in 28% of the cases.

Fifteen percent of the cases had lymphocytic inflammation only. These cases were characterized by increased CD8+ T cells in the crypt epithelium, and all had increased CD4+ T cells in the lamina propria. There was no evidence of acute inflammation (cryptitis, etc.).

Thirty-seven percent of the cases had both neutrophilic and lymphocytic infiltrates. These cases had a relatively high incidence of esosinophilic cryptitis or crypt abscesses and granuloma formation.

Treatment:

Thirty-four of the 41 patients were treated with steroids. The median time between onset of symptoms and initiation of steroid therapy (available for 31 patients) was 8 days (range: 1 to 66 days). Twelve patients treated with steroids had refractory enterocolitis. Refractory enterocolitis was diagnosed when a patient failed to respond to steroid therapy within 7 days (5 patients) or an initial response to steroids followed by a relapse requiring prolonged therapy (7 patients).

Seven patients were not treated with steroids for the following reasons: enterocolitis developed prior to establishing a consistent steroid-based treatment regimen (1 patient), enteritis was diagnosed after reevaluation of a biopsy initially considered normal (1 patient), the patient initially presented with bowel perforation (1 patient), patients had mild symptoms that spontaneously resolved (3 patients), and the enterocolitis resolved with infliximab therapy alone (1 patient).

Four patients with enterocolitis refractory to steroid therapy were treated with a single dose of infliximab at 5 mg/kg. All four patients showed rapid and durable resolution of symptoms after having 10-69 days of prior steroid therapy. See Table 2.

TABLE 2

| Patient | Diagnosis | Doses of MDX-010 (mg/kg) | Symptoms prior to steroids (days) | Steroids prior to infliximab (days) | Infliximab to resolution of enterocolitis (days) |
| --- | --- | --- | --- | --- | --- |
| 1 | Renal cell carcinoma | 3 | — | — | 1 |
| 2 | Malignant melanoma | 5, 5 | 4 | 69 | 1 |
| 3 | Malignant melanoma | 5, 5, 9, 9, 9, 9 | 8 | 40 | 2 |
| 4 | Malignant melanoma | 5, 5, 9 | 8 | 13 | 3 |
| 5 | Malignant melanoma | 5, 9, 9 | 10 | 10 | 2 |

Complications: Four patients suffered colonic perforation secondary to enterocolitis, three patients with renal cell carcinoma and one patient with melanoma. Three of the perforations were in patients with steroid refractory enterocolitis. Perforation occurred after 1, 4, 6 and 6 doses of MDX-010. Two patients died after their perforations. One additional patient with renal cell carcinoma required colectomy for persistent gastrointestinal bleeding secondary to steroid refractory enterocolitis. The incidence of perforation or colectomy in patients treated for renal cell carcinoma was 6.6% (4/61) and 0.7% in patients with melanoma (p=0.032). The mortality rate among patients who developed enterocolitis was 5% (2/41). The mortality rate among all treated patients was 1% (2/198).

Other Immune Mediated Toxicities: Although enterocolitis was the most common Grade III/IV immune mediated toxicity observed with MDX-010 therapy, patients also developed Grade III/IV hypophysitis (13, 7%), dermatitis (8, 4%), arthritis (4, 2%), uveitis (2, 1%), and single cases of hepatitis, nephritis, and aseptic meningitis. In patients who developed enterocolitis, additional Grade III/IV toxicities were: hypophysitis (3), dermatitis (2) and arthritis (1).

Clinical Responses to MDX-010: Of the 198 patients treated, 179 patients were available for evaluation of an objective response. The overall objective response was 15%. Among 34 evaluable patients with enterocolitis, the objective response rate was 41% (14/34). The association of enteocolitis with objective tumor regression was significant for both patients with malignant melanoma and renal cell carcinoma. The objective response rate was 38% for melanoma patients with enterocolitis and 46% for renal cell carcinoma patients with enterocolitis, compared to 12% and 2%, respectively, in patients who did not develop enterocolitis (p=0.0063 for melanoma and p=0.0004 for RCC).

Conclusion: This study showed that high dose steroids were effective for treating enterocolitis induced by anti-CTLA-4 antibody therapy in the majority of patients. Infliximab was an effective therapy for patients with steroid refractory enterocolitis. Infliximab was an effective first line therapy for enterocolitis induced by anti-CTLA-4 antibody therapy in one patient.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Patents, patent applications, publications, product descriptions, and protocols are cited in this application are hereby incorporated by reference in their entireties for all purposes.

The invention claimed is:

1. A method for treating enterocolitis induced by an-anti-CTLA-4 antibody in a patient, comprising administering to the patient an amount of a TNF-α blocking agent effective to treat the enterocolitis, wherein the TNF-α blocking agent is selected from the group consisting of an anti-TNF-α antibody and a TNF receptor fusion protein.

2. The method of claim 1, wherein the anti-CTLA-4 antibody is a human sequence antibody that binds to human CTLA-4.

3. The method of claim 2, wherein the anti-CTLA-4 antibody is 10D1 (ipilimumab).

4. The method of claim 1, wherein the anti-TNF-α antibody is selected from the group consisting of infliximab, certolizumab pegol (CDP870), golimumab and adalimumab.

5. The method of claim 4, wherein the anti-TNF-α antibody is infliximab.

6. The method of claim 5, comprising administering infliximab in a single dose of about 5 mg/kg.

7. The method of claim 1, wherein the TNF-α blocking agent is administered intravenously.

8. The method of claim 1, wherein the anti-CTLA-4 antibody is for the treatment of cancer.

9. The method of claim 8, wherein the cancer is metastatic melanoma or renal cell carcinoma.

10. A method for treating enterocolitis induced by an-anti-CTLA-4 antibody in a patient, comprising administering to the patient an amount of a TNF-α blocking agent effective to treat the enterocolitis, wherein the TNF-α blocking agent is selected from the group consisting of an anti-TNF-α antibody and a TNF receptor fusion protein, wherein the enterocolitis induced by an anti-CTLA-4 antibody is refractory to steroid treatment.

11. The method of claim 10, wherein the anti-CTLA-4 antibody is a human sequence antibody that binds to human CTLA-4.

12. The method of claim 11, wherein the anti-CTLA-4 antibody is 10D1 (ipilimumab).

13. The method of claim 10, wherein the anti-TNF-α antibody is selected from the group consisting of infliximab, certolizumab pegol (CDP870), golimunab, and adalimumab.

14. The method of claim 13, wherein the anti-TNF-α antibody is infliximab.

15. The method of claim 14, comprising administering infliximab in a single dose of about 5 mg/kg.

16. The method of claim 10, wherein the TNF-α blocking agent is administered intravenously.

17. The method of claim 10, wherein the anti-CTLA-4 antibody is for the treatment of cancer.

18. The method of claim 17, wherein the cancer is metastatic melanoma or renal cell carcinoma.

19. The method of claim 1 or 10, further comprising administering an effective amount of a gut-decontaminating antibiotic to the patient.

20. The method of claim 1 or 10, wherein the TNF receptor fusion protein is etanercept.

* * * * *

UNITED STATES PATENT AND TRADEMARK OFFICE
CERTIFICATE OF CORRECTION

PATENT NO. : 7,611,702 B2  Page 1 of 1
APPLICATION NO. : 11/557835
DATED : November 3, 2009
INVENTOR(S) : Steven Fischkoff et al.

It is certified that error appears in the above-identified patent and that said Letters Patent is hereby corrected as shown below:

ON THE TITLE PAGE:

--Item (73) Assignee:   Medarex, Inc., Princeton, NJ (US)-- should read

--Item (73) Assignee:   Medarex, Inc., Princeton, NJ (US)

The Government Of The United States Of America As Represented By The Secretary Of The Department Of Health And Human Services, Rockville, MD (US)--

Signed and Sealed this

Seventh Day of September, 2010

David J. Kappos
*Director of the United States Patent and Trademark Office*